United States Patent [19]

Elliehausen et al.

[11] 4,173,589
[45] Nov. 6, 1979

[54] PURIFICATION OF OXO ALDEHYDES

[75] Inventors: Heinrich Elliehausen, Ludwigshafen; Heinz Hohenschutz, Mannheim; Max Strohmeyer; Juergen Haug, both of Limburgerhof, all of Fed. Rep. of Germany

[73] Assignee: BASF Aktiengesellschaft, Fed. Rep. of Germany

[21] Appl. No.: 844,648

[22] Filed: Oct. 25, 1977

[30] Foreign Application Priority Data

Nov. 6, 1976 [DE] Fed. Rep. of Germany ....... 2650829

[51] Int. Cl.$^2$ ....................... C07C 45/24; C07C 45/08
[52] U.S. Cl. .............................................. 260/604 HF
[58] Field of Search ................ 260/601, 602, 604 HF, 260/601 R

[56] References Cited

U.S. PATENT DOCUMENTS

| | | | |
|---|---|---|---|
| 2,963,514 | 12/1960 | Rehn et al. | 260/604 HF |
| 3,094,564 | 6/1963 | Mertzweiller | 260/604 HF |
| 3,903,172 | 9/1975 | Money et al. | 260/601 |

OTHER PUBLICATIONS

Rosenfeld "Problems of Undesirable Iron Pentacarbonyl Formation" STS Incorp., PLYN, 52 (1): 11-14 (1972).

Primary Examiner—Werren B. Lone
Attorney, Agent, or Firm—Keil & Witherspoon

[57] ABSTRACT

Oxo aldehydes containing iron pentacarbonyl are purified by distilling them in the presence of air.

3 Claims, No Drawings

PURIFICATION OF OXO ALDEHYDES

The present invention relates to an improved process for the purification of oxo aldehydes, ie. aldehydes which have been obtained by hydroformylation (oxo reaction) of olefins.

The hydroformylation of olefins by means of carbon monoxide and hydrogen in the presence of complex compounds containing, in particular, cobalt or rhodium, has been disclosed. Since this reaction is carried out industrially in steel apparatus, the formation of small amounts of iron pentacarbonyl is virtually unavoidable. Even if the aldehydes formed are worked up by distillation, traces of iron pentacarbonyl remain in the distillate and subsequently cause brownish discoloration. Such discolored aldehydes however do not conform to the quality standards required for most end uses, eg. the manufacture of colorless plastics.

U.S. Pat. No. 3,903,172 discloses that iron pentacarbonyl introduced into isobutyraldehyde during the hydroformylation of propylene can be decomposed thermally at 185°–250° C., preferably in the presence of water, so that during the subsequent distillation iron can no longer pass into the distillate. However, this process is uneconomical because of the high decomposition temperatures, which furthermore make it necessary to work under pressure.

It is an object of the present invention to remove the iron pentacarbonyl more simply and more economically when manufacturing pure oxo aldehydes.

We have found that this object is achieved and that oxo aldehydes can be freed from iron pentacarbonyl by distilling them in the presence of air.

This process can in principle be applied to all oxo aldehydes which are distillable under normal pressure, but is particularly suitable for the purification of aldehydes which have been manufactured by hydroformylation of olefins of 2 to 4 carbon atoms. We have found that, contrary to expectation, the losses due to oxidation of the aldehydes are so slight in these cases that they do not adversely affect the economics of this method of purification compared to other methods.

The process has proved very particularly advantageous in the case of butyraldehydes which are obtainable by hydroformylation of propylene and which contain from about 5 to 80 ppm of iron pentacarbonyl in addition to other impurities. Usually, the crude hydroformylation mixture is first subjected to a flash distillation; it is true that this leaves the higher-boiling constituents in the distillation residue, but the iron compound has hitherto passed virtually quantitatively into the distillate consisting of n- and iso-butyraldehyde. If, in accordance with the invention, from 0.01 to 0.1 cubic meter (S.T.P.) of air per gram of iron pentacarbonyl is passed into the feed of crude material to this flash distillation, which conventionally has been carried out substantially with exclusion of air, the iron carbonyl content in the pure fractions of n- and iso-butyraldehyde falls below the limit of detection. The color number (APHA number) determined according to ASTM D 1209-62, which is a measure of the quality of the pure aldehydes, is in this case from about 2 to 4, whilst without air treatment the color numbers are from 30 to 40. These high values, which are unacceptable for practical requirements, are accordingly substantially attributable to the presence of the iron. The losses from oxidized aldehyde are less than 0.7% by weight, and can thus readily be tolerated in view of the substantially greater cost of the conventional methods of purification.

As a result of the addition of air, the iron pentacarbonyl is oxidized to non-volatile iron oxides which remain, together with the higher-boiling constituents, in the residue of the flash distillation. The introduction of the air presents no technical problems. The air can be allowed to bubble, under slightly superatmospheric pressure, into the hot oxo mixture before evaporation of the latter, or can be admixed to the vaporized aldehydes or be introduced directly into the flash column.

EXAMPLE

A crude oxo mixture originating from the hydroformylation of propylene and containing about 6 ppm of iron pentacarbonyl was subjected to a flash distillation at the rate of 10 tonnes per hour, with 1.5 cubic meters (S.T.P.) of air (=0.025 cubic meters (S.T.P.)/g of Fe(CO)$_5$) being introduced before evaporation. Per hour, 8 tonnes of a mixture of n- and iso-butyraldehyde, which no longer contained any iron, were taken off at the top of the column. The color number of the distillate was 2–4. The iron remained quantitatively in the bottom of the flash column, together with the high-boiling constituents. The butyraldehydes were then separated in the conventional manner into their isomers in the second column, the yields, based on the flash distillate, being 74.8% of n-butyraldehyde and 24.8% of iso-butyraldehyde.

Without using air the yields, 24.9 and 74.9% respectively, were, it is true, somewhat higher, but due to the iron content the color numbers were 10 and 30 respectively, and these values are unacceptable for material to be sold or processed further.

We claim:

1. In a process for the purification of oxo aldehydes containing iron pentacarbonyl from the product stream of the manufacture of oxo aldehydes wherein the oxo aldehydes are distilled at normal pressure from the product stream, the improvement comprising:
    distilling the oxo aldehydes containing iron pentacarbonyl in the presence of from 0.01 to 0.10 cubic meter (S.T.P.) of added air per g of iron pentacarbonyl to oxidize the iron pentacarbonyl to non-volatile salts, whereby the oxo aldehydes are freed from iron pentacarbonyl.

2. A process as set forth in claim 1, in which n- and iso-butyraldehyde are purified.

3. A process as set forth in claim 1, wherein the losses due to oxidized aldehyde in the distillaton step are less than 0.7% by weight.

* * * * *